United States Patent [19]
Fletcher et al.

[11] 3,938,035
[45] Feb. 10, 1976

[54] ELECTRICAL CONDUCTIVITY CELL AND METHOD FOR FABRICATING THE SAME

[76] Inventors: James C. Fletcher, Administrator of the National Aeronautics and Space Administration, with respect to an invention of William P. Gilbreath, San Jose, Calif.; Michael J. Adamson, San Jose, Calif.; Alexander G. Fassbender, San Jose, Calif.

[22] Filed: July 16, 1974

[21] Appl. No.: 489,009

[52] U.S. Cl............. 324/30 B; 204/195 R; 215/247
[51] Int. Cl.²......................................... G01N 27/07
[58] Field of Search......... 204/195 R, 279; 73/61 R, 73/61.1 R; 324/30 B; 215/247–249

[56] References Cited
UNITED STATES PATENTS

| | | | |
|---|---|---|---|
| 2,135,386 | 11/1938 | Crabbe | 215/247 |
| 3,760,969 | 9/1973 | Shimamoto et al. | 215/247 |
| 3,784,453 | 1/1974 | Dworkin et al. | 204/286 |

*Primary Examiner*—Alfred E. Smith
*Assistant Examiner*—Wm. H. Punter
*Attorney, Agent, or Firm*—Darrell G. Brekke; Armand G. Morin, Sr.; John R. Manning

[57] ABSTRACT

A flask having a threaded neck and a cap adapted for threaded engagement on the neck. A laminated disc between the cap and the neck forms a gas tight seal and the cap has a central opening that exposes a medial region of the disc. Piercing the disc through the opening are two electrodes, the inner ends of which contact the sample within the flask and the outer ends of which afford connection of test equipment thereto. Cylindric glass tubes are fitted over the external portion of the electrodes to provide physical support therefor; silicone rubber or the like serves to retain the glass cylinders in place and form a gas tight seal between the cylinders and the electrodes. Shrinkable tubing is shrunk over the glass tubes to afford further mechanical support and sealing. A final relatively large diameter shrinkable tube is shrunk over both electrodes and their associated glass cylinders. The support and sealing means for the electrodes is confined to a limited portion of the medial region of the disc so that the remainder of such region can be punctured by a hollow needle to introduce a test sample within the flask.

5 Claims, 4 Drawing Figures

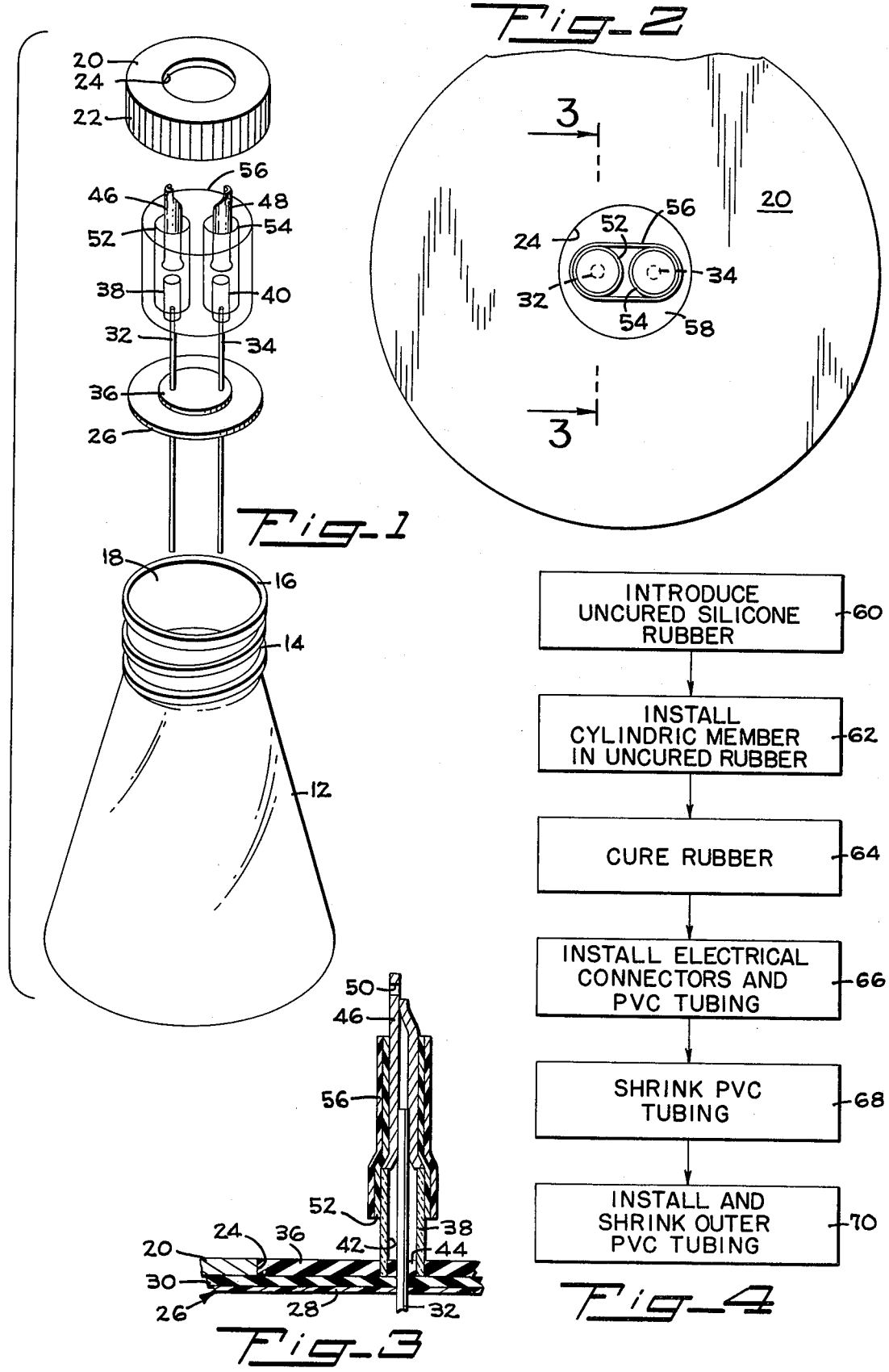

ELECTRICAL CONDUCTIVITY CELL AND METHOD FOR FABRICATING THE SAME

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

This invention relates to a test cell for testing electrical characteristics such as conductivity of a sample and to a method for fabricating such test cell.

2. Description of the Prior Art

Exemplary of the known prior art is Rosenthal, et al. U.S. Pat. No. 2,555,937 which discloses a stopper through which two electrodes extend so that when the stopper is placed in the neck of the test tube the electrodes are immersed in liquid in the test tube. No procedure for introducing fluids into the test tube other than by removing the stopper is disclosed.

U.S. Pat. No. 2,939,070 to Rosenthal discloses individual electrode support structures which are permanently mounted in the wall of an open top container so that when the container is filled with a sample liquid the electrical characteristics thereof can be measured.

Meyer U.S. Pat. No. 3,201,685 discloses a probe that can be immersed in liquid to measure the electrical characteristics thereof.

U.S. Pat. Nos. 2,964,941 (Marsh, et al.); 3,263,224 (Berman, et al.); and 3,286,167 (Gwyn) disclose fittings for supporting two electrodes in a conduit or like path of fluid flow for measuring the characteristics of such fluid.

SUMMARY OF THE INVENTION

The preferred embodiment of the invention that is disclosed in specific detail hereinafter includes a flask and a screw cap for engagement with the neck of the flask. A laminated disc interposed between the cap and the flask neck affords a gas tight seal and the cap is apertured to expose a medial region of the disc. Transpiercing the medial region of the disc are two elongate thin electrodes. At the point where the electrodes pierce the disc a gas tight seal is formed according to the invention. The gas tight seal occupies a limited surface area of the medial region of the disc so that a portion of the disc acts as a septum that can be punctured by a thin needle for introducing sample material into the flask without opening the same. The disc has a lamina of self-sealing material such as silicone rubber so that upon removal of the hollow needle the sample within the flask cannot escape and contaminates cannot enter the flask from the exterior thereof.

The object of the present invention is to provide a test cell that permits introduction of samples into and removal of samples from the test cell without opening the test cell. This object is achieved because of the provision of the above mentioned laminated disc and confinement of the electrodes and their supporting structure to a limited portion of the exposed area of the disc.

Another object of the invention is to provide a test cell of the character to which reference has been made above that is simple and inexpensive to fabricate. This object is achieved because fabrication of the electrode supporting and sealing structure is achieved without special tools, jigs, or molds.

A feature and advantage flowing from achievement of the above stated object is that numerous test chambers employing electrodes of an appropriate material can be retained in inventory or can be fabricated quickly.

A further object of the present invention is to provide a method for fabricating a test cell of the type to which reference has been made above which method can be carried out without special equipment by relatively unskilled personnel.

The foregoing together with other objects, features and advantages will be more apparent after referring to the following specification and the accompanying drawing.

BRIEF DESCRIPTION OF THE DRAWING

FIG. 1 is an exploded view of a test cell according to the present invention.

FIG. 2 is a top plan view of the cap and electrode support structure according to the invention.

FIG. 3 is a fragmentary cross sectional view at enlarged scale taken along line 3—3 of FIG. 2.

FIG. 4 is a block diagram showing the sequence of steps for a method of fabricating a test cell according to the invention.

DESCRIPTION OF THE PREFERRED EMBODIMENT

Referring more particularly to the drawing reference numeral 12 indicates a conventional Erlenmeyer flask that has a threaded neck 14 at the top of which is a shoulder 16 which circumscribes an opening 18. A screw cap having a top planar wall 20 from the periphery of which depends an interiorly threaded skirt 22 is provided, the threads interior of skirt 22 size to engage the threads on neck 14 of flask 12. Planar wall 20 is formed with an aperture or opening 24. A laminated disc 26 has a shape such that it fits within the cap and rests on shoulder 16 in spanning relation of opening 18. Disc 26 has an inner lamina 28 which is formed of a material such as teflon that is inert to the sample within flask 12 and an outer layer 30 of silicone rubber or the like that is self-sealing. It is thus seen that when the cap is threaded onto neck 14 with disc 26 interposed between the lower surface of planar cap wall 20 and shoulder 16 that a medial region of disc 26 is exposed through opening 24. The elements described up to this point are commercially available, one such commercial product being known by the trademark Reacti-Flask.

In fabricating a test cell according to the present invention two spaced apart holes are formed, such as by drilling, through the medial region of disc 26. Through the holes are passed elongate electrodes 32 and 34, the holes being somewhat smaller than the outer diameter of the electrodes so as to inhibit leakage therethrough. For example, in one structure designed according to the invention the outside diameter of electrodes 32 and 34 is 2 mm and the diameter of the holes is 1.5 mm. The electrodes are positioned so that a portion of the electrodes extends into flask 12 and a portion extends above planar cap wall 20. When the cap and disc 26 are in place on neck 14 there is a concavity formed which concavity is bounded on the bottom by the medial region of the upper surface of disc 26 and the side wall of opening 24 in the cap. Into this concavity is introduced a curable rubber-like material, such as RTV silicone rubber, such material in its cured condition being indicated in FIG. 3 at 36. As is well known RTV silicone rubber is in a liquid condition before curing and after curing is a rubber-like material. According to the present invention a pair of insulative hollow cylindric support members 38 and 40 are installed on the exterior ends of electrodes 32 and 34. The cylindric members can be glass tubing having an inside diameter or bore 42 somewhat larger than the outside diameter of the electrodes and a length less than the amount by which the electrodes extend above disc 26. Cylindric members 38 and 40 are moved downward, while rubber-like material 36 is in the uncured or liquid date, toward disc 26 until the cylindric members are at least partially immersed in the uncured rubber-like material. As seen in FIG. 3, there is an annular space between cylindric member and electrode 32 so that a portion of the rubber-like material is extruded into the annular space and forms a seal around the electrode. Such portion of the rubber-like material is indicated in FIG. 3 at 44. Electrodes 32 and 34 and their associated cylindric members 38 and 40 are retained in the position shown in FIG. 3 until the RTV silicone rubber material cures whereupon a gas tight seal is formed as well as a mechanical support.

In one test cell designed according to the invention cylindric spacers 38 and 40 are formed of glass tubing having a length of about one centimeter and an outside diameter of 4 mm. When the cylindric members are fixed by virtue of the curing of rubber-like material 36 a pair of electrical connectors 46 and 48 is telescoped over the protruding ends of electrodes 32 and 34. Electrical connectors 46 and 48 can be made of tubular spring bronze or the like so that when telescoped over the respective electrodes 32 and 34 a good electrical and mechanical connection is formed. The upper ends of the electrical connectors can be provided with a hole 50 for facilitating connection of test circuit wiring to the electrodes.

With the electrical connectors in place tubular members 52 and 54 are placed over the electrical connectors and the upper portion of cylindric spacers 38 and 40. Tubular members 52 and 54 are constructed of flexible heat shrinkable material, such as PVC, so in their untreated condition they fit easily over the electrical connectors. When they are heated, however, the tubular members 52 and 54 shrink radially inward so as to compress the electrical connectors and retain them in place. Final assembly of the test cell according to the invention is achieved by placing a relatively larger heat shrinkable tubular member 56 over both of the previously installed shrunk tubular members 52 and 54, after which the assembly is again subjected to heat so as to cause relatively large tubular member 56 to shrink radially inward and reinforce the entire electrode structure.

Although the above described assembly operations are performed while the cap is engaged on neck 14 of the flask, the cap and electrode assembly can be removed after fabrication so that flask 12 can be cleaned or samples can be introduced into or removed from the interior of the flask.

FIG. 2 shows an important feature of the present invention, namely: that the electrode support structure occupies only a limited area of the medial region of disc 26 that is aligned with cap opening 24. Because the electrode structure occupies only a limited portion of the medial region there is a margin 58 of the medial region that is accessible for piercing by a hollow needle or the like so that samples can be introduced into or removed from the interior of the flask without removing the cap and without interrupting the tests that are being conducted. Because of the presence of rubber-like layer 30 on cap 26 and the presence of rubber-like material 36 thereover, the exposed margin acts as a septum in that it self seals upon removal of the hollow needle therefrom.

Because the test cell and electrode support structure of the invention can be fabricated without special tooling or jigs, a plurality of cap-electrode assemblies can be inventoried. This is important in certain tests because the material of which electrodes 32 and 34 are constructed is of importance. For example, one exemplary test for which the cell of the present invention is particularly suited is a test to determine the compatibility of copper and aluminum in freon. In such test electrode 32 is constructed of copper and electrode 34 is constructed of aluminum and liquid freon is placed within flask 12. A second test in which electrodes 32 and 34 are constructed of graphite is made in liquid freon, and the comparison of the conductivity between the two tests produces useful data. Moreover because inner disc layer 28 is constructed of inert material, e.g. teflon, its integrity is not impaired during performance of the tests.

Another test with respect to which the cell of the present invention is particularly useful is for observation of changes in electrical conductivity of hydrazine fuels during exposure to various metals and contaminates. Hydrazine fuels and various test metals and contaminates are introduced into flask 12 and the conductivity changes if any are observed by apparatus connected to electrical connectors 46 and 48.

The method for fabricating a test cell of the present invention can be more fully appreciated by reference to the block diagram of FIG. 4. After electrodes 32 and 34 are pierced through the holes in disc 26, the uncured rubber like material is poured into the concavity bounded by the disc and the wall of opening 24, such pouring or introducing step being indicated at 60 in FIG. 4. While the rubber like material is in its uncured state, cylindric glass tubes 38 and 40 are inserted over the electrodes and immersed in the uncured rubber material as indicated at 62. With the parts retained in the position described next above the rubber is cured which in the case of RTV silicone rubber is achieved by exposing the rubber to air for an extended period. The curing step is indicated at 64 in FIG. 4. Next electrical connectors 46 and 48 are telescoped over the protruding ends of the electrodes and flexible tubular members 52 and 54 are installed thereover, such steps being shown at 66 in FIG. 4. The parts assembled as described to this point are then subjected to an elevated temperature so that the PVC tubing is shrunk thus securing the electrical connectors in mechanical and electrical contact with the electrodes. Finally, the outer heat shrinkable tubing 56 is installed and heated so that it is shrunk so as to embrace tightly the electrodes and their associated components. In FIG. 4 the last mentioned step is indicated at 70. When step 70 has been completed the apparatus is ready for use, and because the sealing structure for the electrodes is confined to a limited area of the medial region of disc 26, the marginal area 58 of the disc is accessible for introduction and removal of samples to the flask interior.

Thus it will be seen that the present invention provides an extremely simple test cell structure and a method for forming the same that can be quickly accomplished without special fixtures or jigs. Accordingly, a large inventory of the electrode supporting structures can be stored so as to achieve virtually any test conditions. Although one embodiment of the invention has been shown and described, it will be obvious that other adaptations and modifications can be made without departing from the true spirit and scope of the invention.

What is claimed is:

1. A test cell for testing the electrical characteristics of a sample comprising an impervious container for the sample, said container having an opening and a shoulder circumscribing said opening, a laminated disc having an area corresponding to that of the opening, said disc having an inner lamina and an outer lamina, said inner lamina being inert to the sample and sealable on said shoulder, said outer lamina being formed of self sealing material fixed to said inner lamina, means for retaining said disc in spanning relation of said opening, said retaining means acting to seal the periphery of said inner lamina against said shoulder and to expose a medial region of said outer lamina exterior of said container, first and second electrodes transpiercing said disc at a portion of the medial region thereof, and means for supporting said electrodes in gas tight relation to said disc, said supporting means being limited so as to afford access to a portion of the medial region of said disc so that the medial region can be pierced to afford introduction of the sample into said container, wherein said supporting means comprises first and second cylindric members having central bores of a diameter larger than the outer diameter of said electrodes, said cylindric members being disposed on respective said electrodes so that the outer ends of the electrodes extend through said bores, said cylindric members having axial extremities secured to said outer lamina, and means intermediate the surface of said electrodes and said bores for forming a gas tight seal therebetween.

2. A test cell according to claim 1 wherein said gas tight seal forming means comprises a silicone rubber like compound.

3. A test cell according to claim 2 including first and second flexible tubular members having a length exceeding that of said cylindric members, said tubular members being shrunk fit over respective said electrodes and cylindric members.

4. A test cell according to claim 3 including a third flexible tubular member having a length corresponding to said first and second tubular members, said third tubular member being shrunk fit in circumscribing relation of both said first and second tubular members.

5. A test cell according to claim 3 including first and second electrical connectors, said electrical connectors defining openings for telescopic engagement with the outer ends of respective said electrodes, said first and second shrunk fit tubular members extending to a medial region of respective said connectors to retain said connectors onto respective said electrodes, there being a protruding portion of said connectors protruding exterior of said tubular members to afford circuit connection thereto.

* * * * *